(12) United States Patent
Dorr et al.

(10) Patent No.: US 11,364,174 B2
(45) Date of Patent: Jun. 21, 2022

(54) COLD THERAPY DYNAMIC HAND SPLINT SYSTEM

(71) Applicant: ARIZONA BOARD OF REGENTS ON BEHALF OF ARIZONA STATE UNIVERSITY, Scottsdale, AZ (US)

(72) Inventors: Brandon Arthur Dorr, Tucson, AZ (US); Kay Wing, Phoenix, AZ (US); Christopher Wiedeman, Tempe, AZ (US); Cole Hunter, Tempe, AZ (US); Jeffrey Kleim, Scottsdale, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 695 days.

(21) Appl. No.: 16/207,132

(22) Filed: Dec. 1, 2018

(65) Prior Publication Data
US 2019/0167510 A1    Jun. 6, 2019

Related U.S. Application Data

(60) Provisional application No. 62/593,708, filed on Dec. 1, 2017.

(51) Int. Cl.
*A61H 9/00* (2006.01)
*A61F 5/05* (2006.01)
*A61F 5/058* (2006.01)

(52) U.S. Cl.
CPC ....... *A61H 9/0092* (2013.01); *A61F 5/05866* (2013.01); *A61H 2201/0214* (2013.01);
(Continued)

(58) Field of Classification Search
CPC .......... A61H 9/0092; A61H 2201/0214; A61H 2201/0242; A61H 2201/0285;
(Continued)

(56) References Cited

U.S. PATENT DOCUMENTS 3,164,152 A    1/1965  Vere Nicoll
3,811,434 A *  5/1974  Jacobson ............ A61F 5/05816
                                                  128/DIG. 20
(Continued)

FOREIGN PATENT DOCUMENTS

WO       2013169363 A2    11/2013

OTHER PUBLICATIONS

African Oxygen Ltd., "Material Safety Data Sheet (MSDS) R134A" [online], AFROX, Jul. 2011 [retrieved Aug. 18, 2020 from archive. org, as it appeared on 2017-09-97], retrieved from the internet <https://web.archive.org/web/20170907100648/http://www.afrox.co.za/internet.global.corp.zaf/en/images/R134a266_27719.pdf?v=2.0>.

(Continued)

*Primary Examiner* — Tu A Vo
(74) *Attorney, Agent, or Firm* — Rodney J. Fuller; Booth Udall Fuller, PLC (57) ABSTRACT

A cold therapy dynamic hand splint system including an electric pump, a sleeve, an inflatable bladder, a refrigeration device, and a fluid reservoir. The sleeve includes a fluid-tight cavity filled with a cold fluid pressurized by the pump, and is wrapped around the forearm of a user. The inflatable bladder has an expanded state where the bladder is charged with the fluid pressurized by the pump and chilled by the refrigeration device, and a collapsed state where the bladder is substantially empty. The bladder is small enough that a portion fits inside a palm of a contracted spastic hand while in the collapsed state, and large enough to press the spastic hand open when the bladder is in the expanded state. The fluid is maintained within a therapeutic temperature range, and is in fluidic communication with the sleeve and the bladder through the pump.

20 Claims, 5 Drawing Sheets

(52) U.S. Cl.
CPC ............... *A61H 2201/0242* (2013.01); *A61H 2201/0285* (2013.01); *A61H 2201/1635* (2013.01); *A61H 2201/5007* (2013.01); *A61H 2201/5071* (2013.01); *A61H 2201/5082* (2013.01)

(58) Field of Classification Search
CPC .... A61H 2201/1635; A61H 2201/5007; A61H 2201/5071; A61H 2201/5082; A61F 5/05866
See application file for complete search history.

(56) References Cited

U.S. PATENT DOCUMENTS

| | | | |
|---|---|---|---|
| 4,157,713 A | 6/1979 | Clarey | |
| 4,182,320 A * | 1/1980 | Sweeney | A61F 5/05816 128/DIG. 20 |
| 4,274,399 A * | 6/1981 | Mummert | A61H 1/0288 601/40 |
| 4,281,647 A * | 8/1981 | Antypas | A61F 5/05816 128/DIG. 20 |
| 4,619,250 A * | 10/1986 | Hasegawa | A61H 1/0288 128/DIG. 20 |
| 4,677,971 A | 7/1987 | Lindemann | |
| 4,709,694 A | 12/1987 | O'Connell | |
| 4,765,320 A | 8/1988 | Lindemann et al. | |
| 4,807,606 A * | 2/1989 | Hasegawa | A61H 1/0288 128/DIG. 20 |
| 4,883,462 A * | 11/1989 | Williamson | A61H 9/0078 604/540 |
| 4,907,574 A * | 3/1990 | Hollerbach | A61H 1/0266 128/DIG. 20 |
| 5,005,824 A * | 4/1991 | Eichel | A63B 23/16 482/44 |
| 5,020,515 A * | 6/1991 | Mann | A61F 5/05816 128/DIG. 20 |
| 5,152,740 A * | 10/1992 | Harkensee | A61F 5/05816 128/DIG. 15 |
| 5,383,827 A * | 1/1995 | Stern | A63B 21/00178 482/47 |
| 5,437,620 A * | 8/1995 | Shelly | A61F 5/05866 601/40 |
| 5,531,668 A * | 7/1996 | Mann | A63B 23/16 482/44 |
| 5,916,186 A * | 6/1999 | Turto | A61F 5/0118 602/20 |
| 6,881,219 B1 | 4/2005 | Agarwal et al. | |
| 6,945,988 B1 * | 9/2005 | Jones | A61F 7/10 607/108 |
| 7,001,352 B2 | 2/2006 | Farrell et al. | |
| 10,350,105 B2 * | 7/2019 | Eriksson | A61F 5/012 |
| 2004/0210176 A1 * | 10/2004 | Diana | A61H 9/0078 601/151 |
| 2008/0132816 A1 * | 6/2008 | Kane | A61H 7/001 601/152 |
| 2009/0048649 A1 * | 2/2009 | Peret | A61H 9/0057 607/100 |
| 2009/0069731 A1 * | 3/2009 | Parish | A61F 7/0085 601/150 |
| 2010/0042027 A1 * | 2/2010 | Hirata | A61F 5/05816 601/151 |
| 2010/0139294 A1 * | 6/2010 | Lowe | F25D 17/02 62/56 |
| 2011/0172749 A1 * | 7/2011 | Christensen | A61F 7/02 607/104 |
| 2011/0190675 A1 * | 8/2011 | Vess | A61H 9/0092 601/152 |
| 2011/0276082 A1 * | 11/2011 | Fehring | A61H 1/0285 606/204 |
| 2014/0142473 A1 * | 5/2014 | Lowe | A61F 7/02 601/18 |
| 2014/0221880 A1 * | 8/2014 | Yang | A61F 7/02 601/18 |
| 2015/0148196 A1 * | 5/2015 | Hanks | A61H 1/0292 482/8 |
| 2015/0148710 A1 | 5/2015 | Towe et al. | |
| 2015/0366695 A1 * | 12/2015 | Galloway | A61F 5/012 602/6 |
| 2016/0081843 A1 * | 3/2016 | Eriksson | A61F 5/05866 602/6 |
| 2016/0184126 A1 * | 6/2016 | Boezaart | A61F 5/0585 602/13 |
| 2016/0252110 A1 * | 9/2016 | Galloway | A61H 1/024 60/327 |
| 2018/0000626 A1 * | 1/2018 | Deren | A61F 5/05816 |

OTHER PUBLICATIONS

Amarine-Made, "Amanne-made Automatic High Pressure Diaphragm Water Pump DC 12V 3.6L/min for General Industry,Vehicles,Agricultural,Boat" [online], Amazon, 2019 [retrieved on Sep. 20, 2019, reviews suggest availability at east as early as Oct. 2017], retrieved from the internet: <URL:https://www.amazon.com/dp/B0717BLFW9/ref=asc_df_B0717BLFW95335103/?tag=hyprod-%2020&creative=395033&creativeASIN=B0717BLFW9&linkCode=df0&hvadid=198107334619&h%.

American National Standard., "Accessible and Usable Buildings and Facilities", International Code Council, Oct. 1998, 102 pages.

ASTM International., "Manual on the Use of Thermocouples in Temperature Measurement", American Society for Testing and Materials, 1970, 261 pages <DOI:10.1520/STP470-EB>.

ASTM International., "Standard Guide for Characteristics for Extremity Splints", ASTM, Jul. 2015, Designation: F1555-94, 2 pages <DOI:10.1520/F1555-94R15>.

ASTM International., "Standard Guide for Expression of Temperature", ASTM,May 2016, Designation: E1594-16, 3 pages <DOI:10.1520/E1594-16>.

ASTM International., "Standard Specification for Poly(Vinyl Chloride) (PVC) Plastic Flexible Concealed WaterContainment Membrane", ASTM, Jan. 2018 [last previous edition approved in 2012], Designation: D4551-17, 9 pages <DOI:10.1520/D4551-17>.

ASTM International., "Standard Specification for Temperature Monitoring Equipment", ASTM, Oct. 2013, Designation: F2362-03, 44 pages <DOI:10.1520/F2362>.

ASTM International., "Standard Terminology Relating to Medical and Surgical Materials and Devices", ASTM, Dec. 2010, Designation: F2809-10, 92 pages <DOI:10.1520/F2809-10>.

ASTM International., "Standard Test Method for Measuring the Performance of Personal Cooling Systems Using Physiological Testing", ASTM, Jul. 2016, Designation: F2300-10, 8 pages <DOI:10.1520/F2300-10R16>.

ASTM International., "Standard Test Method for Steady-State Thermal Transmission Properties by Means of the Heat Flow Meter Apparatus", ASTM, Jul. 2017, Designation: C518-17, 16 pages <DOI:10.1520/C0518-17>.

Better Braces, "Aircast Shoulder Cryo/Cuff w/Cooler" [online], Better Braces, 2016 [retrieved Aug. 18, 2020 from archive.org, as it appeared on Dec. 4, 2016], retrieved from the internet <https://web.archive.org/web/20161204185505/https://www.betterbraces.com/aircast-shoulder-cryo-cuff>.

Beyond Stroke, "Spasticity" [online], Beyondstroke.com, 2016 [retrieved on May 15, 2020 from archive.org, as it appeared on Jan. 11, 2017], retrieved from the internet: <URL:https://web.archive.org/web/20170111235012/http://www.beyondstroke.ca/physical-challenges/spasticity.aspx>.

Blick Art Materials, "MSDS for #57319—Velcro Sticky Back" [online], Dick Blick, Aug. 2012 [retrieved Aug. 18, 2020], retrieved from the internet <http://www.dick-blick.com/msds/DBH_57319XXXX.pdf>.

BRIO, "BPA-Free Reusable Plastic Water Bottle Gallon Jug Container—Made in USA", Amazon, 2019 [retrieved on Sep. 20, 2020, reviews suggest availability at least as early as Aug. 2017], retrieved from the internet: <URL:https://www.amazon.com/Gallon-Plastic-Reusable- (56) References Cited

OTHER PUBLICATIONS

Bottle-%20Container/dp/B01LZQG1XE/ref=sr_1_cc_1?s=aps&ie=UTF8&qid=1516047056&sr=1-1-%20catcorr&keywords=2+gallon+water+container>.

Computer Aided Technology, "How Much Does SOLIDWORKS Cost?" [online], Computer Aided Technology, Apr. 2015 [retrieved Aug. 18, 2020], retrieved from the internet <https://www.cati.com/blog/2015/04/how-much-does-solidworks-cost/>.

CynKen, "CynKen 10mm Metric Chrome Flexible Head Ratchet Action Wrench Spanner Nut Tool" [online], Amazon, 2019 [retrieved on Aug. 18, 2020, first available Mar. 2017], retrieved from the internet <https://us.amazon.com/CynKen-Metric-Flexible-Ratchet-Spanner/dp/B06XDD35B2>.

Dorr, B. et al., "CryoRelease: Relief for Spasticity" (updated title: CryoRelease: Temperature Regulating Dynamic Splint for Spasticity Relief), presented at the Biomedical Engineering Symposium ASU School of Biological and Health Systems Engineering on Dec. 1, 2017.

Dynatronics, "510(k) Summary of Safety and Effectiveness for Dynatron Peltier Thermostim", Accessdata FDA, Jan. 2014 [retrieved on Aug. 10, 2020 from archive.org, as it appeared on Feb. 7, 2017], retrieved from the Internet <https://web.archive.org/web/20170207161522/https://www.accessdatafda.gov/cdrh_docs/pdf13/k132057.pdf>.

Elbio Co Ltd, "510(k) Summary for COOLSKIN", Accessdata FDA, Jun. 2009 [retrieved on Aug. 10, 2020 from archive.org, as it appeared on Feb. 15, 2017], retrieved from the internet <https://web.archive.org/web/20170215132500/https://www.accessdata.fda.gov/cdrh_docs/pdf8/k083008.pdf>.

El-Maksoud, G. et al., "Efficacy of cold therapy on spasticity and hand function in children with cerebral palsy", Journal of Advanced Research, Oct. 2011 (available online Mar. 2011), vol. 2, No. 4, pp. 319-325 <DOI:10.1016/jare.2011.02.003>.

Energy Star., "Program Requirements Product Specification for Water Coolers", Eligibility Criteria, May 2013, Version 2.0, 13 pages.

Lee, S. et al., "Effect of cold air therapy in relieving spasticity: applied to spinalized rabbits", Spinal Cord, Mar. 2002, vol. 40, pp. 167-173 <DOI:10.1038/sj.sc.3101279>.

Power Probe, "Butane Soldering Kit Tools Equipment Hand Tools" [online], Amazon, 2019 [retrieved on Sep. 20, 2019, first availability date not indicated on site], retrieved from the internet: <URL:https://www.amazon.com/Butane-Soldering-Tools-Equipment-%20Hand/dp/B00DJFFNBE/ref=sr_1_8?s=lawn-garden&ie=UTF8&qid=1515884810&sr=1-%208&keywords=soldering+kit>.

Qubicaamp Worldwide, "Material Safety Data Sheet: PVC Compounds Pellet and Powder" [online], Georgia Gulf Chemicals and Vinyls, LLC, Feb. 2005 [retrieved Aug. 18, 2020], retrieved from the internet <https://www.qubicaamf.com/msds-forms/forms/gutter-coverboard-capping-en.pdf>.

Rexqualis, "REXQualis UNO Project Super Starter Kit with Tutorial and UNO R3 Compatible with Arduino IDE" [online], Amazon, 2019 [retrieved on Sep. 20, 2019, date first listed on Amazon Aug. 2017], retrieved from the Internet: <URL:https://www.amazon.com/Development-Membrane-%20Joystick-Receiver-Detailed/dp/B074WMHLQ4/ref=sr_1_6?ie=UTF8&qid=1516041582&sr=8-%206&keywords=arduino+kit>.

Saebo, "Recover From Your Stroke With Saebo" [online], Saebo, 2017 [retrieved Aug. 18, 2020 from archive.org, as it appeared on Oct. 23, 2017], retrieved from the internet <https://web.archive.org/web/20171023070456/https://www.saebo.com/>.

Sciencelab, "Material Safety Data Sheet Water MSDS" [online], ScienceLab, May 2013 [retrieved Aug. 18, 2020 from archive.org, as it appeared on Nov. 9, 2017], retrieved from the internet <https://web.archive.org/web/20171119174702/http://www.sciencelab.com/msds.php?msdsId=9927321>.

Uline., "Tabletop Impulse Sealer—8"" [online], Tabletop Poly Bag Sealers—Impulse, 2019 [retrieved on Sep. 20, 2019, first availability date not indicated on site], retrieved from the internet: <URL:https://www.uline.com/Product/Detail/H-163/Poly-Bag-%20Sealers/Tabletop-Impulse-Sealer-8?pricode=WA9036&gadtype=pla&id=H-%20163&gclid=EAlalQobChMlyeL974TW2AIVB8NkCh3LWw1ZEAQ-YASABEgKCx_D_BwE&%20gclsrc=aw.ds>.

Uxcell, "uxcell 1/4BSP Male Thread 10mm Dia Brass Hose Barb Fittings Couplers Connectors 4pcs" [online], Amazon, 2020 [retrieved on Aug. 18, 2020, first available Feb. 2017], retrieved from the internet <https://www.amazon.com/uxcell-Thread-Fittings-Couplers-%20Connectors/dp/B06WGWR72P/ref=sr_1_6?ie=UTF8&qid=1516045987&sr=8-%206&keywords=10mm+barb>.

Uxcell, "uxcell Silicone Tube 10mm ID X 13mm OD 6.56 Feet Flexible Silicone Rubber Tubing Water Air Hose Pipe Translucent for Pump Transfer" [online], Amazon, 2019 [retrieved on Sep. 20, 2019, first available Nov. 2016], retrieved from the Internet: <URL:https://www.amazon.com/uxcell-Translucent-Silicone-%20Resistant-Meters/dp/B01N52GBTI/ref=sr_1_3?s=industrial&ie=UTF8&qid=1516049411&sr=1-%203&keywords=10mm+hose>.

Velcro, "Velcro Brand All-Purpose Straps | Strong & Reusable | Perfect for Fastening Wires & Organizing Cords | Black, 18in × 1in | 2 Count" [online], Amazon, 2019 [retrieved on Sep. 20, 2019, first available May 2006], retrieved from he interner: <URL:https://www.amazon.com/VELCRO-Brand-%20Purpose-Straps-Elastic/dp/B000TGX0HK?th=1>.

Miller Electric, "Miller 951413 60SX Arcstation Fully Loaded " [online], Amazon, 2020 [retrieved Aug. 18, 2020, first available Jul. 2011], retrieved from the internet <https://www.amazon.com/Miller-951413-Arcstation-Fully-Loaded/dp/B005BUS560>.

* cited by examiner

COLD THERAPY DYNAMIC HAND SPLINT SYSTEM

RELATED APPLICATIONS

This application claims the benefit of U.S. provisional patent application 62/593,708, filed Dec. 1, 2017, titled "Cold Therapy Dynamic Hand Splint," the entirety of the disclosure of which is hereby incorporated by this reference.

TECHNICAL FIELD

Aspects of this document relate generally to cold therapy hand splints.

BACKGROUND

Muscle spasticity is a chronic condition in which affected muscles are constantly activated, leaving joints immobile. Over 12 million people suffer from spasticity worldwide, often as the result of neurodegenerative diseases and disorders, such as cerebral palsy, stroke, and multiple sclerosis, or other brain or spinal cord injuries. The contractions caused by spasticity drastically inhibit the ability to use ones hands or feet for most daily activities. Prolonged contraction can lead to the permanent shortening of muscles and tendons, or contractures, which often requires surgery to remedy. Over half of post stroke-patients with spasticity develop contractures, because the condition is often left untreated.

Muscle spasticity greatly inhibits the effectiveness of physical therapy for neurodegenerative diseases, and while treatments for spasticity exist, they tend to be time-consuming, require in-person professional care, or carry adverse effects.

The efficacy of physical therapy, a preferred treatment for spasticity, is often tied to patient compliance and efforts outside of therapy. Available home treatments and devices, such as conventional hand splints, dynamic extension spring systems, and ice water therapy, do no provide much short term relief, and are often difficult to implement without assistance.

The complicated implementation and lack of relief provided by conventional home treatments for spasticity has traditionally resulted in low user compliance. As physical therapy is most effective once the spasticity is temporarily relieved, physical therapists spend a large amount of each session working out the patient's spasticity. This activity not only tires the patient, but also erodes valuable physical therapy time. Low user compliance at home reduces the overall speed and efficacy of physical therapy, and has contributed to the high rate of contractures requiring surgical intervention.

SUMMARY

According to one aspect, a cold therapy dynamic hand splint system comprises an electric pump, and a sleeve comprising PVC and having two fluid-tight cavities filled with a cold fluid pressurized by the pump. The sleeve also has a first edge and a second edge opposite the first edge, the first and second edges releasably coupled to each other through two straps. The first and second edges are sized to extend along a majority of a forearm of a user when the sleeve is wrapped around the forearm. The cold therapy dynamic hand splint system further comprises an inflatable bladder comprising PVC and having an expanded state wherein the bladder is charged with the cold fluid pressurized by the pump and a collapsed state wherein the bladder is substantially empty. The inflatable bladder is sized such that it is small enough that at least a portion of the bladder fits inside a palm of a contracted spastic hand of the user while the bladder is in the collapsed state and large enough that the portion is larger then the palm of the contracted spastic hand when the bladder is in the expanded state. The cold therapy dynamic hand splint system also comprises a refrigeration device that is thermoelectric, and a fluid reservoir comprising the cold fluid. The fluid is in thermal contact with the refrigeration device and maintained within a therapeutic temperature range. Furthermore, the fluid is in fluidic communication with the two fluid-tight cavities of the sleeve and the inflatable bladder through the electric pump, at least one valve, and at least one hose.

Particular embodiments may comprise one or more of the following features. The inflatable bladder may be torus-shaped when in the expanded state. The inflatable bladder may be semi-cylindrical when in the expanded state. The cold therapy dynamic hand splint system may further comprise a control system communicatively coupled to the pump and/or the refrigeration device. The control system may have a thermal sensor, a pressure sensor, and/or a processor configured to operate the refrigeration device to keep the fluid within the therapeutic temperature range. The processor may be configured to operate the pump to drive the inflatable bladder from the collapsed state to the expanded state by gradually increasing a pressure within the inflatable bladder, and/or maintain the expanded state for a predetermined amount of time. The therapeutic temperature range may be between 0° C. and 20° C.

According to another aspect of the disclosure, a cold therapy dynamic hand splint system comprises an electric pump, and a sleeve comprising a fluid-tight cavity filled with a cold fluid pressurized by the pump. The sleeve also has a first edge and a second edge opposite the first edge. The first and second edges are releasably coupled to each other. The first and second edges are sized to extend along a majority of a forearm of a user when the sleeve is wrapped around the forearm. The cold therapy dynamic hand splint system also comprises an inflatable bladder having an expanded state wherein the bladder is charged with the cold fluid pressurized by the pump and a collapsed state wherein the bladder is substantially empty. The inflatable bladder is sized such that it is small enough that at least a portion of the bladder fits inside a palm of a contracted spastic hand of the user while the bladder is in the collapsed state and large enough that the portion is larger then the palm of the contracted spastic hand when the bladder is in the expanded state. The cold therapy dynamic hand splint system further comprises a refrigeration device, and a fluid reservoir coupled to the refrigeration device and comprising the cold fluid. The fluid is in thermal contact with the refrigeration device and maintained within a therapeutic temperature range. Furthermore, the fluid is in fluidic communication with the fluid-tight cavity of the sleeve and the inflatable bladder through the electric pump and at least one hose. Particular embodiments may be modified or adapted such that the inflatable bladder is directly coupled to the sleeve.

According to yet another aspect of the disclosure, a cold therapy dynamic hand splint system comprises an electric pump, and a sleeve comprising a cold source. The sleeve is sized to extend along a majority of a forearm of a user when the forearm is worn and the cold source is in thermal contact with the forearm. The cold therapy dynamic hand splint system also comprises an inflatable bladder having an expanded state wherein the bladder is charged with a cold fluid pressurized by the pump and a collapsed state wherein the bladder is substantially empty. The inflatable bladder is sized such that it is small enough that at least a portion of the bladder fits inside a palm of a contracted spastic hand of the user while the bladder is in the collapsed state and large enough that the portion is larger then the palm of the contracted spastic hand when the bladder is in the expanded state. The cold therapy dynamic hand splint system further comprises a fluid reservoir comprising the cold fluid. The fluid is within a therapeutic temperature range and in thermal contact with the contracted spastic hand through the inflatable bladder while the bladder is in the expanded state. Furthermore, the fluid is in fluidic communication with the inflatable bladder through the electric pump and at least one hose.

Particular embodiments may comprise one or more of the following features. The cold source may comprise at least one sealed cold pack releasably coupled to the sleeve. Each of the at least one cold packs may be substantially equal in length to the majority of the forearm. The fluid reservoir may comprise an opening to receive ice water. The cold fluid may be ice water. The cold therapy dynamic hand splint system may further comprise a refrigeration device coupled to the fluid reservoir and the pump, and may be thermal contact with the cold fluid. The refrigeration device may maintain the cold fluid within the therapeutic temperature range. The cold source may be a fluid-tight cavity filled with the cold fluid pressurized by the pump. The fluid-tight cavity may be in fluidic communication with the fluid reservoir through the pump and/or at least one hose.

Aspects and applications of the disclosure presented here are described below in the drawings and detailed description. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

The use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the example embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

The invention will hereinafter be described in conjunction with the appended drawings, where like designations denote like elements, and.

DETAILED DESCRIPTION

This disclosure, its aspects and implementations, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented, but have been omitted for purposes of brevity.

While this disclosure includes a number of embodiments in many different forms, there is shown in the drawings and will herein be described in detail particular embodiments with the understanding that the present disclosure is to be considered as an exemplification of the principles of the disclosed methods and systems, and is not intended to limit the broad aspect of the disclosed concepts to the embodiments illustrated.

Muscle spasticity is a chronic condition in which affected muscles are constantly activated, leaving joints immobile. Over 12 million people suffer from spasticity worldwide, often as the result of neurodegenerative diseases and disorders, such as cerebral palsy, stroke, and multiple sclerosis, or other brain or spinal cord injuries. The contractions caused by spasticity drastically inhibit the ability to use ones hands or feet for most daily activities. Prolonged contraction can lead to the permanent shortening of muscles and tendons, or contractures, which often requires surgery to remedy. Over half of post stroke-patients with spasticity develop contractures, because the condition is often left untreated.

Muscle spasticity greatly inhibits the effectiveness of physical therapy for neurodegenerative diseases, and while treatments for spasticity exist, they tend to be time-consuming, require in-person professional care, or carry adverse effects.

The efficacy of physical therapy, a preferred treatment for spasticity, is often tied to patient compliance and efforts outside of therapy. Available home treatments and devices, such as conventional hand splints, dynamic extension spring systems, and ice water therapy, do no provide much short term relief, and are often difficult to implement without assistance.

The complicated implementation and lack of relief provided by conventional home treatments for spasticity has traditionally resulted in low user compliance. As physical therapy is most effective once the spasticity is temporarily relieved, physical therapists spend a large amount of each session working out the patient's spasticity. This activity not only tires the patient, but also erodes valuable physical therapy time. Low user compliance at home reduces the overall speed and efficacy of physical therapy, and has contributed to the high rate of contractures requiring surgical intervention.

Contemplated herein is a cold therapy dynamic hand splint system (hereinafter hand splint system) that combines cryotherapy and kinesiotherapy into a single device that is effective and easy to use. This hand splint system can relieve hand spasticity at home, and is easy to operate, even using contracted spastic hands. The hand splint system simultaneously cools the hand and arm while stretching the hand and fingers. This greatly reduces spasticity within a reasonable time period (e.g. in under 10 minutes in some cases), preparing a user for further physical therapy, providing quick relief at home, and providing the user with a greater degree of independence.

The hand splint system contemplated herein makes use of cryotherapy that does not have the disadvantages of conventional treatment methods. Traditional methods, such as submersion in an ice water bath, have been effective in temporarily relieving spasticity, but the discomfort of the cold temperatures results in low user compliance. The hand splint system employs temperatures above 0° C. that are much more tolerable, while still being effective.

Advantageous over traditional treatment devices, the hand splint system contemplated herein may be used on a hand that is contracted. Traditional treatment devices, such as conventional dynamic splints and spring-loaded gloves, make use of mechanisms that hold a spastic hand open, but can only be used after the hand has been opened. Not only are they difficult to use, they cannot be employed as a pre-therapy treatment, opening the hand in preparation for physical therapy. As will be discussed below, the disclosed hand splint system may be used on a contracted spastic hand, prior to opening.

Furthermore, conventional treatment devices make use of kinesiotherapy, or cryotherapy, but never both. The hand splint systems contemplated herein provide both, using a coolant as a pneumatic fluid to stretch appendages and as a medium for heat transport to cool the hand. Simultaneously providing kinesiotherapy and cryotherapy increases both the speed and efficacy of the treatment.

According to various embodiments, the hand splint system consists of an inflatable bladder and a sleeve, which are filled with cooled fluid, and which interface with the user's arm and hand to provide controlled cooling. The fluid is pumped from a reservoir, through a refrigeration device, and into the inflatable bladder and sleeve. The inflatable bladder is inserted into the palm of a spastic hand while deflated. The sleeve and bladder are filled with cooled fluid by the pump. The inflatable bladder expands, exerting gentle pressure (user adjustable) on the contracted spastic hand, opening it while providing cooling to the hand and arm.

The contemplated hand splint system is advantageous over convention system in a number of ways. It provides cooling in a way that does not require a mess or direct contact with the liquid. This allows for a simpler relief process that still adequately cools the hand and forearm. Additionally, it uses an inflation mechanism to stretch the hand, while simultaneously cooling it. Most conventional devices use springs with plastic joints and stiff materials to flex and manipulate the hand, making them difficult to use and uncomfortable. In comparison, the inflatable bladder mechanism allows the device to be contoured to the user, rather than the user to the device.

Figure 1:
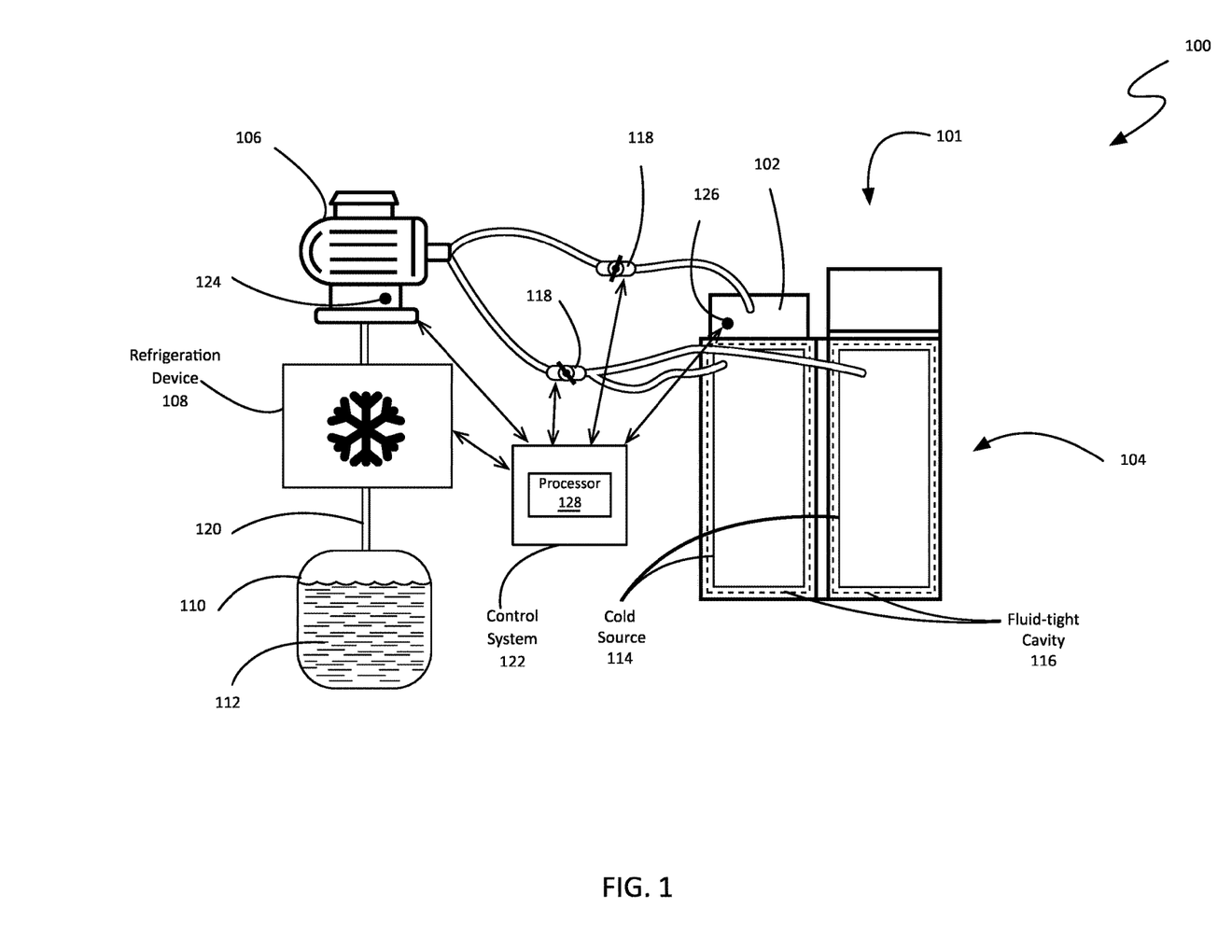
FIG. 1 is a schematic view of a cold therapy dynamic hand splint system.

FIG. 1 is a schematic view of a non-limiting example of a cold therapy dynamic hand splint system 100. As shown, the system 100 includes the hand splint 101, made up of an inflatable bladder 102 and a sleeve 104. The splint 101 is in fluid communication with a reservoir 110 through an electric pump 106 and a refrigeration device 108. As shown, the system 100 may also make use of valves 118 and hoses 120.

The inflatable bladder 102 is able to collapse small enough to fit in the palm of a contracted spastic hand. According to various embodiments, the inflatable bladder 102 is in fluidic communication with the reservoir 110 through the pump 106 and refrigeration device 108, and configured to receive fluid 112 pressurized by the pump 106 and chilled by the refrigeration device 108. The fluid 112 inflates the bladder 102, such that it expands and grows large enough to stretch the spastic hand open. The operation of the inflatable bladder 102 will be discussed in greater detail with respect to FIGS. 3A and 3B. The shape and material of the inflatable bladder 102 will be discussed in greater detail with respect to FIGS. 4A and 4B, below.

According to various embodiments, the sleeve 104 chills the users wrist and arm. In some embodiments, the sleeve 104 may cover a majority of a users forearm, while in other embodiments it may extend further to cover a portion of the users bicep.

As shown, the sleeve 104 comprises a cold source 114 to chill the tissue of the wrist and arm. In some embodiments, the cold source 114 may be integral with the sleeve 104, while in others it may be removable. Additionally, in some embodiments the cold source 114 may be a single unit spread across the sleeve 104, while in others it may be multiple, separate units. For example, the cold source 114 of the non-limiting example shown in FIG. 1 comprises two fluid-tight cavities 116 that are coupled to the fluid reservoir through hoses, receiving the same cold fluid 112 as the inflatable bladder 102. The sleeve 104 will be discussed in greater detail with respect to FIGS. 2 and 5, below.

According to various embodiments, the pump 106 may be a high-pressure liquid pump. In some embodiments, the pump 16 maybe voltage controlled, allowing a user or an automated control system to modify the pump intensity to provide the proper pressure. In other embodiments, the pump intensity may be controlled using any other method known in the art.

Controlling and modifying the output intensity of the pump 106 allows for the gradual increase of pressure exerted on the spastic hand by the inflatable bladder 102. This allows the user to set the pace at which the hand is opened, allowing for greater comfort and adaptability to the variations among patients.

In some embodiments, the pump 106 recirculates the fluid through the system, which may be advantageous in embodiments that actively cool the fluid. In other embodiments, the pump 106 may simply increase the internal pressure of the system without moving the fluid in a circuit. A non-circulating implementation may be used in embodiments without a refrigeration device, and instead rely on a supply of fluid already chilled (e.g. ice water, etc.).

According to various embodiments, the pump 106 only needs to be powerful enough to create sufficient pressure within the inflatable bladder 102 to exert enough force on the spastic hand to gently open it, in light of ambient pressure. In some embodiments, said pressure is approximately 60-70 kPa above atmospheric. In other embodiments, the pressure may be limited to 40 psi.

The refrigeration device 108 is in thermal contact with the fluid, and is tasked with achieving and maintaining a fluid temperature within a therapeutic range. In the context of the present description and the claims that follow, a therapeutic temperature range is a range of temperatures that provide a degree of relief to a spastic hand while avoiding or minimizing the discomfort often associated with cryotherapy. According to some embodiments, a therapeutic range may be between 0° C. and 20° C. In other embodiments, the therapeutic range may be between 15° C. and 20° C. In some embodiments, maintaining the fluid within the therapeutic temperature range may be sufficient to cool the arm and hand tissue to 30° C. in 3-6 minutes.

In some embodiments, the refrigeration device 108 may be a thermoelectric device. As a specific example, a thermoelectric device may comprise a one or more thermoelectric plates, sandwiched between a cooling block and a heat sink. As an option, the heat sink may have one or more fans. The fluid 112 is in thermal contact with the cooling block, either in direct contact or passing through a structure coupled to the cooling block (e.g. a high surface area lattice, etc.). Thermoelectric devices can quickly arrive at a target temperature, and are typically much quieter and more compact than traditional compressor-based refrigeration devices. Having studied the teachings disclosed herein, those skilled in the art will recognize and appreciate that other refrigeration systems may be employed in other embodiments. As an option, in some embodiments the pump 106 and the refrigeration device 108 may be combined into a single unit or device.

According to various embodiments, the fluid 112 may be any coolant having a high thermal capacity, a low viscosity, and does not pose a danger to the user or the device itself (e.g. non-toxic, non-corrosive, chemically inert, etc.). Examples include, but are not limited to, water, deionized water, glycol/water solutions, and the like. Some embodiments may employ liquid temperatures below 0° C., to speed up the overall process. The fluid 112 used in such embodiments may comprise antifreeze compounds including, but not limited to, ethylene glycol, diethylene glycol, propylene glycol, and betaine. Other coolants may be used as well, as is known in the art.

In the context of the present description and the claims that follow, a fluid reservoir 110 is a volume capable of holding a fluid to be pumped into the splint 101. In some embodiments, the reservoir 110 may be a separate container coupled to the refrigeration device 108 or pump 106 through a conduit such as a hose 120. In other embodiments, the reservoir 110 may be directly coupled to the pump 106 or refrigeration device 108, providing a more compact (but potentially unwieldy) system 100 overall.

In some embodiments, the fluid reservoir 110 may be sealed, creating a closed system that would be best adapted to use with a refrigeration device 106. In other embodiments, the fluid reservoir 110 may have a lid or other opening through which fluid, particularly already chilled fluid such as ice water, may be introduced (or removed). For example, in one embodiment, the fluid reservoir 110 may be a container or vessel (e.g. a 2-gallon plastic container, etc.) that can be filled with ice water.

As shown in FIG. 1, the system 100 may comprise one or more valves 118. According to various embodiments, one or more valves 118 may be used to restrict or allow the flow of fluid into the sleeve 104 and inflatable bladder 102. The ability to divert the flow may be advantageous, as it may allow the use of a weaker pump 106. For example, a valve 118 may be actuated to cause the fluid-tight cavities 116 of the sleeve 104 to inflate first, thereafter allowing the full force of the pump to be directed to the inflatable bladder 102, which must fight against the contracted spastic hand. In some embodiments, the valve(s) 118 may be manually operated, while in others they may be electric, and may be operated by an automation system.

In some embodiments, the hand splint system 100 may be operated manually, with the user adjusting operational parameter such as the intensity of the pump 106 and the temperature of the fluid 112 using conventional controls known in the art, such as knobs. As an option, the controls may be adapted for operation using a contracted spastic hand.

In other embodiments, one or more operational parameters of the hand splint system 100 may be automated using a control system 122. As shown in FIG. 1, the control system 122 may be communicatively coupled to the pump 106, the refrigeration device 108, and one or more (electronic) valves 118, such that it may control their operation. The control system 122, comprising a processor 128, may also be communicatively coupled to one or more sensors, including but not limited to thermal sensors 124, pressure sensors 126, or sensors that detect or measure an electrical signal (e.g., an electrical signal produced by the user's nervous system in response to a change in hand or arm contraction, relaxation, or other change in conformation).

The control system 122 may be used to reduce the need for interaction with the user. Contracted spastic hands typically have difficulty operating control interfaces like knobs and dials. In some embodiments, the control system 122 may monitor the temperature of the fluid 112, and operate the refrigeration device 108 such that the fluid 112 is kept within a therapeutic temperature range. In other embodiments, the control system 122 may be configured to operate the pump 106 to gradually increase the force exerted on the spastic hand by the expanding inflatable bladder 102, to prevent discomfort while still achieving therapeutic goals. In still other embodiments, the control system 122 may automatically start a timer when treatment commences, and automatically shutting off after a predetermined amount of time has elapsed, or the bladder 102 has expanded to an intended endpoint and held that shape for a predetermined amount of time. The processor 128 of the control system 122 may be configured to perform one or more of these functions, or take over other aspects of the treatment. As previously mentioned, at-home compliance is necessary for effective treatment through physical therapy; the use of a control system 122 makes the hand splint system 100 that much easier to use, and more likely to be implemented on a regular basis.

In some embodiments, the control system 122 may follow a predefined set of instructions and parameters. In other embodiments, the control system 122 may operate within a set of rules and protocols, but use information obtained from one or more sensors to ensure treatment goals are met.

As a specific example, a control system 122 may be configured to determine the current volume of the inflatable bladder 102, and use that information to guide the control of the pump 106. Variations in the degree of contraction of a spastic hand (i.e. variations in interval between treatment sessions, other environmental factors that influence degree of spasticity, etc.) mean that the pressure exerted one day may not be sufficient (or may be too much) the next. An adaptive control system 122 such as this may further increase user compliance, requiring fewer decisions on the part of the user.

Figure 2:
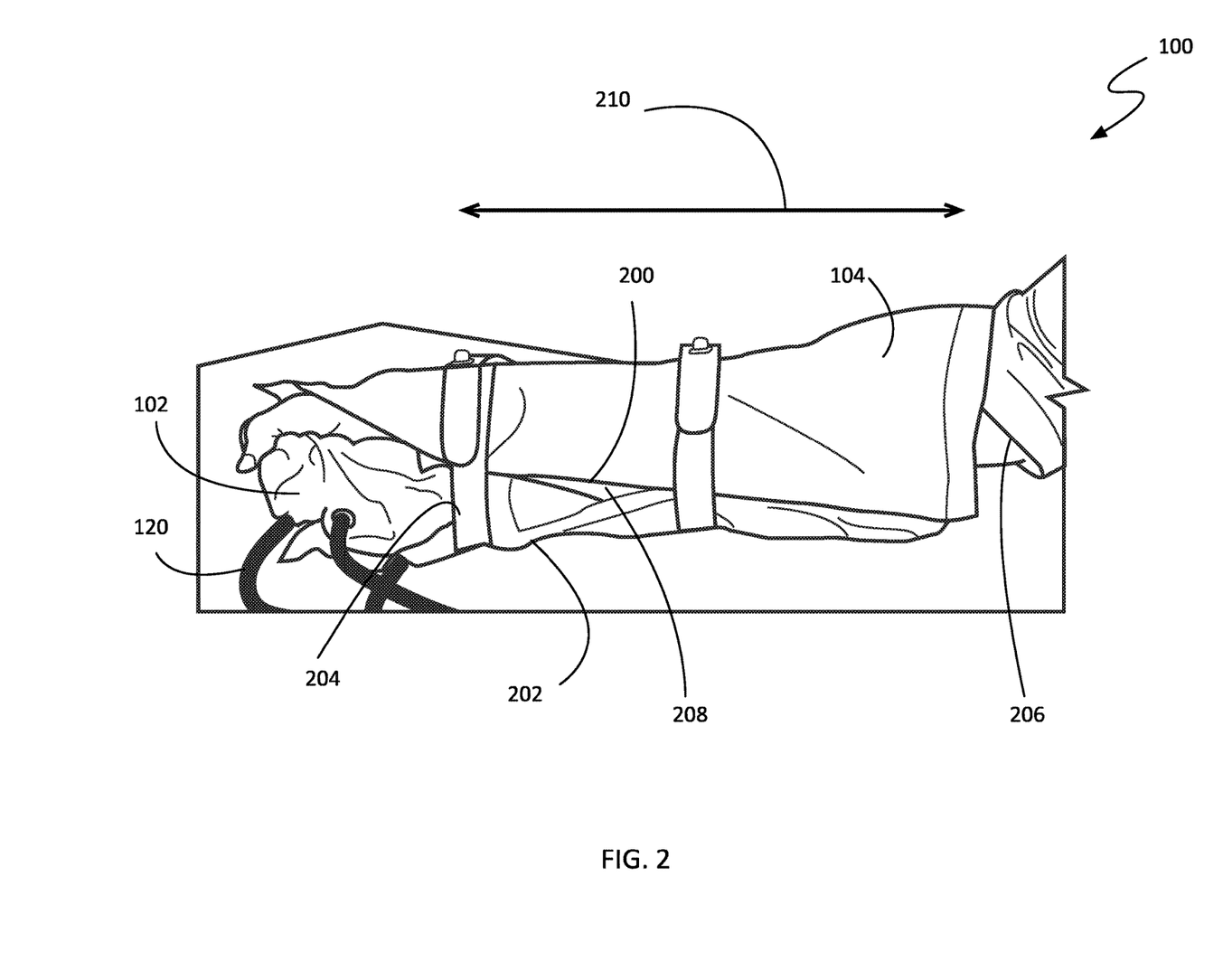
FIG. 2 is a perspective view of a cold therapy dynamic splint system in use.

FIG. 2 is a perspective view of a non-limiting example of a hand splint system 100 in use. It should be noted that the refrigeration device 108 and pump 106 are not depicted in FIG. 2.

As shown, the sleeve 104 is wrapped around the forearm 208 of a user 206. According to various embodiments, the sleeve 104 may be rectangular in shape, having a first edge 200 and a second edge 202 that is opposite the first edge 200. A sleeve 104 such as this may be referred to as a flat sleeve, in that it can be positioned as a single flat layer when not in use. In other embodiments, the sleeve 104 may have a permanent hollow in the middle, into which a user 206 inserts their arm. These sleeves may be referred to as hollow sleeves, in contrast to flat sleeves.

As discussed above, the sleeve 104 may be sized such that it covers (and chills) at least a majority 210 of the forearm 208. In some embodiments, the sleeve 104 may extend all the way to the lower bicep. In the case of a rectangular sleeve 104 such as the one depicted in FIG. 2, the first 200 and second 202 edges extend along at least a majority 210 of the forearm 208. Other embodiments may employ flat sleeves 104 having a shape other than rectangular.

According to various embodiments, a flat sleeve such as the rectangular sleeve 104 shown in FIG. 2 may be attached to an arm for treatment by wrapping around the arm so the first and second edges are near each other. The sleeve 104 may then be secured to the arm using one or more couplings, which may include straps (such as the straps 204 shown in FIG. 2), clasps, snaps, hook-and-loop panels, or any other coupling known in the art.

In embodiments making use of a hollow sleeve, the sleeve 104 may simply be slid on. This may be easier to use for a user with spasticity, though potentially at the cost of adaptability to different size arms. Embodiments making use of fluid-tight cavities 116 within the sleeve 104 may further be secured to the arm by expanding with fluid enough to gently squeeze the arm. In other embodiments, hollow sleeves may be secured to the arm using cinching couplings such as straps and the like, to facilitate contact and thermal transfer between the arm and the sleeve 104. Furthermore, in embodiments where the sleeve 104 is cooled by fluid 112 provided by a pump 106, the sleeve 104 is typically secured to the users in an empty, or substantially empty, state, making the sleeve 104 lighter and easier to manipulate.

Figure 3A:
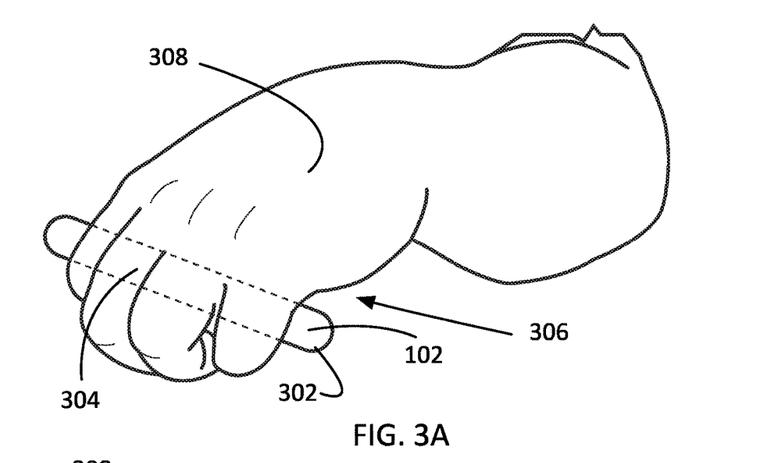
FIG. 3A is a perspective view of a spastic hand contracted around an inflatable bladder in a collapsed state.
Figure 3B:
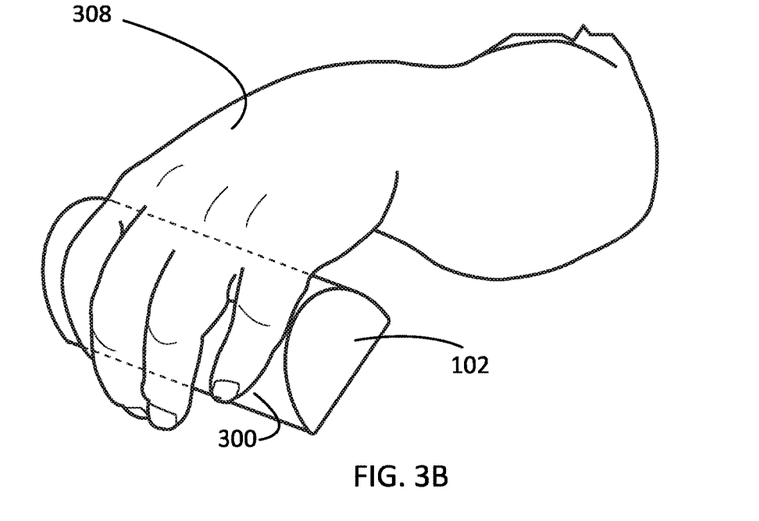
FIG. 3B is a perspective view of the spastic hand of FIG. 3A opened by the inflatable bladder in an expanded state.

FIGS. 3A and 3B are perspective views of a spastic hand 308 and a non-limiting example of an inflatable bladder 102. Specifically, FIG. 3A is a perspective view of a spastic hand 308 contracted around an inflatable bladder 102 in a collapsed state 302, and FIG. 3B is a perspective view of the spastic hand 308 of FIG. 3A opened by the inflatable bladder 102 in an expanded state 300.

One of the many advantages the hand splint system 100 has over conventional treatment devices is that it can be used to open a contracted spastic hand 308, while conventional devices require the hand to already be opened. According to various embodiments, the application of the hand splint system 100 to a contracted spastic hand 308 comprises inserting at least a portion 304 of the inflatable bladder 102 into the palm 306 of the spastic hand while the bladder 102 is in a collapsed state 302, meaning it is substantially empty of fluid 112. It should be noted that while in some embodiments only a portion 304 of the bladder 102 is inserted into the palm, in other embodiments the entire bladder 102 may fit in the palm while in a collapsed state 302.

In the context of the present description and the claims that follow, substantially empty means "effectively" empty of fluid 112; while some traces of fluid 112 may remain, they are not enough to meaningfully increase the volume of the cavity 116 or bladder 102. Furthermore, in the context of the present description and the claims that follow, to be inserted into the palm 306 of a contracted spastic hand 308 means to be positioned in the immediate vicinity of the palm, within any volume of space bounded by the contracted digits of the hand.

After a portion 304 of the inflatable bladder 102 has been inserted into the palm 306, it is charged with cold fluid 112 pressurized by the pump 106, driving the bladder 102 to an expanded state 300. In the context of the present description and the claims that follow, the expanded state 300 of an inflatable bladder 102 is when the portion 304 inserted into the palm 306 has expanded to be larger than the palm 306 and has begun to exert outward force on the contracted digits. Further inflation of the bladder 102 will continue to open the hand, while simultaneously providing relief via cryotherapy.

Hands come in many shapes and sizes. Furthermore, the nature of spasticity varies from one individual to another. The inflatable bladder 102 that perfectly fits one person may be useless to another. While in some embodiments the inflatable bladder 102 may be affixed to, or even integral with, the sleeve 104, in other embodiments the inflatable bladder 102 may be separate from the sleeve 104.

Figure 4A:
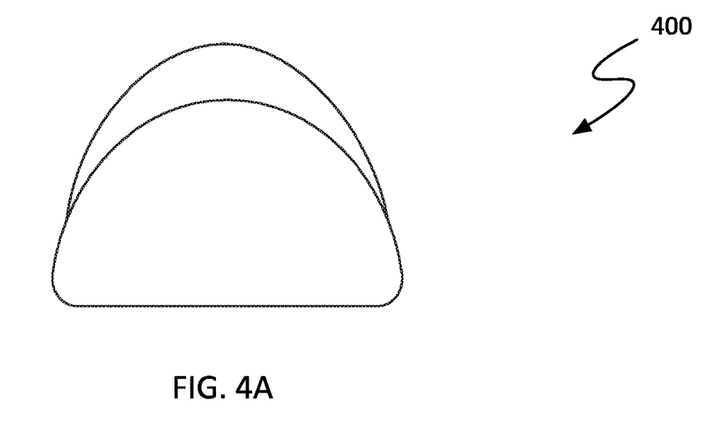
FIGS. 4A and 4B are perspective views of different embodiments of the inflatable bladder.
Figure 4B:
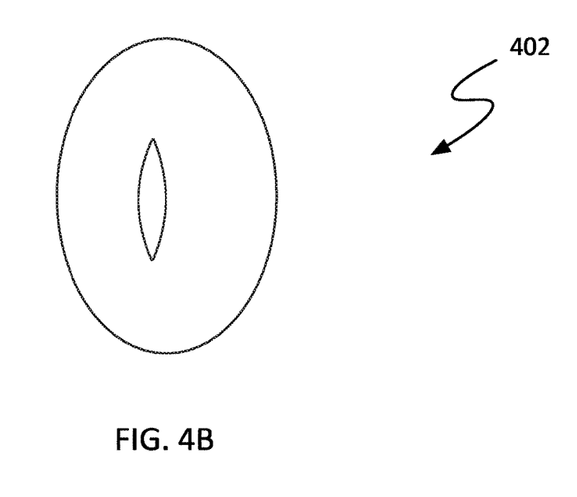

Inflatable bladders 102 may come in different sizes and shapes. FIGS. 4A and 4B show perspective views of non-limiting examples of semi-cylindrical 400 and torus-shaped 402 inflatable bladders 102, respectively. It should be noted that the following discussion of bladder shapes is done in the context of the bladders 102 being in an expanded state 300.

FIG. 4A shows a non-limiting example of an inflatable bladder 102 that is semi-cylindrical 400. Such a shape may be advantageous for insertion into the palm of a severely contracted hand. Being essentially linear in shape, the semi-cylindrical bladder 400 (in its collapsed state 302) will be easy to slide into the palm through a gap in the contracted grip.

FIG. 4B shows a non-limiting example of an inflatable bladder 102 that is torus-shaped 402. A torus-shaped bladder 102 may be advantageous for use with a hand with diminished grip strength. According to various embodiments, the hand may be slid through the central hole of a torus-shaped 402 bladder while in the collapsed state 302, then pulled back so a portion of the torus has been inserted into the palm. The torus shape helps keep the bladder in place while the inflation is underway. As an added benefit, upon inflation, the torus-shaped bladder 102 allows thermal contact with the chilled fluid 112 to both the inside and outside of the hand. It should be noted that other embodiments may make use of any other shape, including but not limited to disc-shaped, hand-shaped, spherical, and the like.

The inflatable bladder 102 is constructed of material that is fluid-tight (i.e. impermeable or nearly impermeable to the fluid), strong enough to resist the passive forces of a spastic hand without rupturing, yet thin enough to allow for sufficient thermal transfer between the hand and the fluid 112. In some embodiments, the inflatable bladder 102 may be composed of polyester. As a specific example, in one embodiment the inflatable bladder 102 may be composed of 0.6 mm polyester. In other embodiments, the inflatable bladder 102 may be composed of PVC. In still other embodiments, the inflatable bladder 102 (and sleeve 104) may be composed of any other safe, flexible, fluid-tight material known in the art.

The non-limiting examples of inflatable bladders 102 shown in FIGS. 4A and 4B are intended to be in contact with the spastic hand, but not directly coupled. In some embodiments, the bladder 102 may rest against the palm and digits of a spastic hand, while in other embodiments, the bladder 102 may be attached to one or more digits, to facilitate its extension. For example, in some embodiments the bladder 102 may comprise one or more loops or pouches into which fingers or fingertips may be inserted while in the collapsed state, which aid in the opening of the hand as the bladder 102 is inflated.

Figure 5:
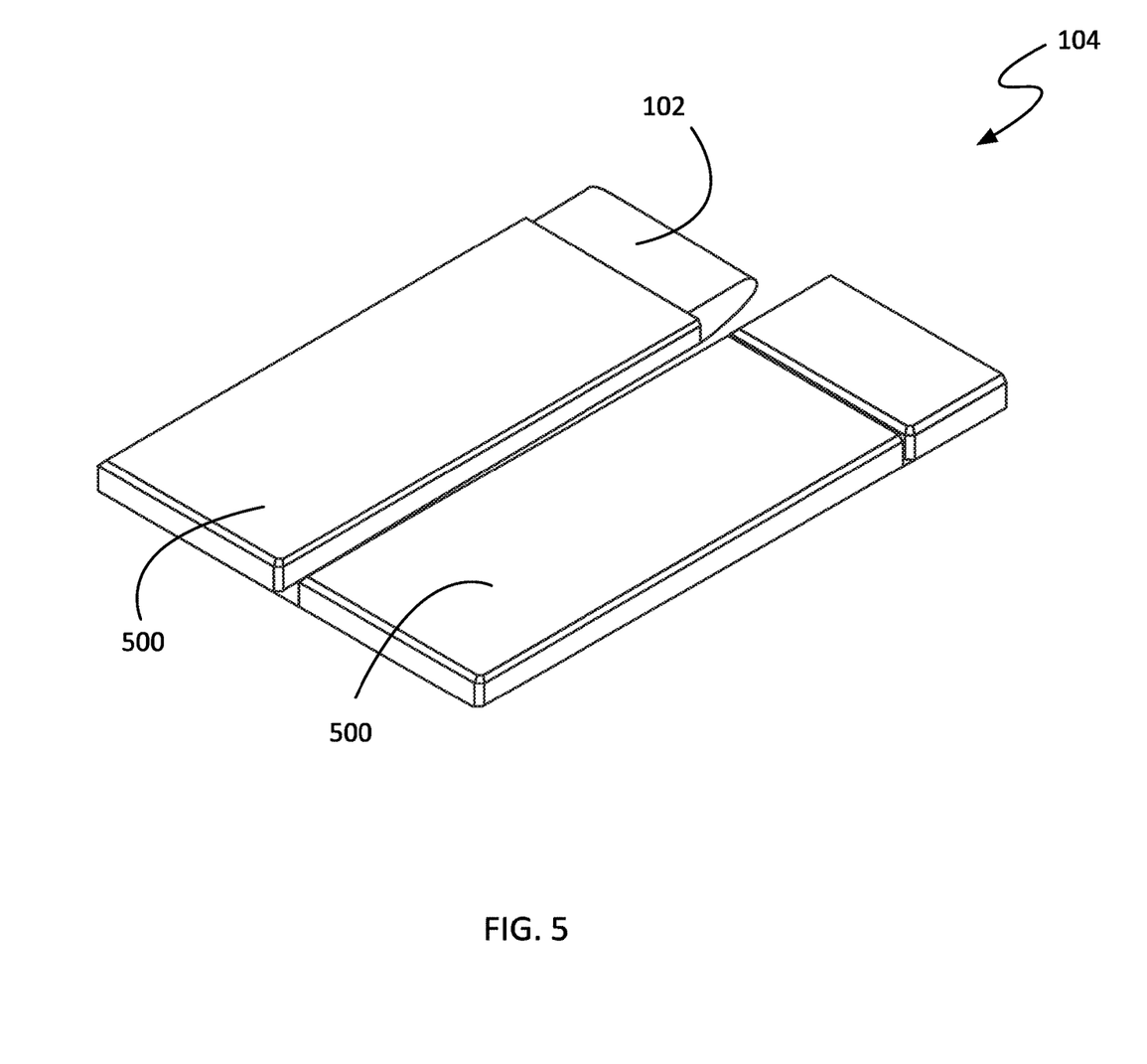
FIG. 5 is a perspective view of a sleeve.

FIG. 5 is a perspective view of a non-limiting example of a flat sleeve 104 with an attached inflatable bladder 102. As mentioned above, in some embodiments, the cold source 114 of the sleeve 104 may differ from the chilled fluid 112 pumped into the bladder 102. The sleeve 104 shown in FIG. 5 is a non-limiting example of such an implementation, making use of multiple sealed cold packs 500 which are prepared through exposure to a cold environment such as a freezer. The use of a non-fluid cold source 114 in the sleeve 104 presents a number of advantages, such as reducing the required volume of fluid, and capacity of refrigeration device and pump 106, resulting in a smaller device overall.

Where the above examples, embodiments and implementations reference examples, it should be understood by those of ordinary skill in the art that other hand splint devices and systems and manufacturing devices and examples could be intermixed or substituted with those provided. In places where the description above refers to particular embodiments of a hand splint device and customization methods, it should be readily apparent that a number of modifications may be made without departing from the spirit thereof and that these embodiments and implementations may be applied to other hand splint device customization technologies as well. Accordingly, the disclosed subject matter is intended to embrace all such alterations, modifications and variations that fall within the spirit and scope of the disclosure and the knowledge of one of ordinary skill in the art.

Any dimensions presented in this document are for example only and not a limitation on the scope of this disclosure. It will be understood that embodiments are not limited to the specific components disclosed herein, as virtually any components consistent with the intended operation of the method or system may be utilized. Accordingly, for example, although particular materials, structures, and couplings may be disclosed, such components may comprise any shape, size, style, type, model, version, class, grade, measurement, concentration, material, weight, quantity, or the like consistent with the intended operation of a hand splint device.

Accordingly, the components defining any hand splint device embodiment may be formed of any of many different types of materials or combinations thereof that can readily be formed into shaped objects provided that the components selected are consistent with the intended operation of a hand splint device embodiment. For example, the components can comprise one or more: polymers such as thermoplastics (such as ABS, Fluoropolymers, Polyacetal, Polyamide; Polycarbonate, Polyethylene, Polysulfone, or other similar material), thermosets (such as Epoxy, Phenolic Resin, Polyimide, Polyurethane, Silicone, or other similar material); glasses (such as quartz glass), carbon-fiber, aramid-fiber, any combination thereof, or other similar material; composites; metals, such as zinc, magnesium, titanium, copper, lead, iron, steel, carbon steel, alloy steel, tool steel, stainless steel, brass, tin, antimony, pure aluminum, 1100 aluminum, aluminum alloy, or other similar materials; alloys, such as aluminum alloy, titanium alloy, magnesium alloy, copper alloy, any combination thereof, or other similar materials; and one or more of any of the above with one or more or other similar material.

Various hand splint device embodiments may be manufactured using conventional procedures as added to and improved upon through the procedures described here. Some components may be manufactured simultaneously and integrally joined with one another, while other components may be purchased pre-manufactured or manufactured separately and then assembled with the integral components.

Accordingly, manufacture of these components separately or simultaneously may involve one or more of extrusion, pultrusion, vacuum forming, injection molding, blow molding, resin transfer molding, casting, forging, cold rolling, milling, drilling, reaming, turning, grinding, stamping, cutting, bending, welding, soldering, hardening, riveting, punching, plating, or other similar process. If any of the components are manufactured separately, they may then be coupled with one another in any suitable manner, such as with adhesive, a weld, a fastener (e.g., a bolt, a nut, a screw, a nail, a rivet, a pin), wiring, any combination thereof, and/or the like for example, depending on, among other considerations, the particular material forming the components.

Upon reading the teachings of this specification, those with ordinary skill in the art will appreciate that, under certain circumstances, considering issues such as changes in technology, user requirements, etc., a variety of fastening devices may be used to affix, couple, or releasably couple, (as those words are used herein) one or more components of the present disclosure. These fastening devices may comprise one or more of the following: adhesives, belts, bolts, buckles, clasps, latches, locks, screws, snaps, clamps, connectors, couplings, ties, or other fastening means yet to be developed.

Likewise, upon reading the teachings of this specification, those with ordinary skill in the art will appreciate that, under certain circumstances, considering issues such as changes in technology, subject requirements, etc., a variety of fastening devices, such as adhesives, belts, bolts, buckles, clasps, latches, locks, screws, snaps, clamps, connectors, couplings, ties or other fastening means yet to be developed may be used in lieu of—or in conjunction with—any of the fasteners or fastening means discussed above.

Where the above examples, embodiments and implementations reference examples, it should be understood by those of ordinary skill in the art that other hand splint devices and examples could be intermixed or substituted with those provided. In places where the description above refers to particular embodiments of cold therapy dynamic hand splint systems, it should be readily apparent that a number of modifications may be made without departing from the spirit thereof and that these embodiments and implementations may be applied to other to spasticity treatment technologies as well. Accordingly, the disclosed subject matter is intended to embrace all such alterations, modifications and variations that fall within the spirit and scope of the disclosure and the knowledge of one of ordinary skill in the art.

What is claimed is:

1. A cold therapy dynamic hand splint system, comprising:
   an electric pump;
   a sleeve comprising polyvinyl chloride (PVC) and having two fluid-tight cavities filled with a cold fluid pressurized by the pump, the sleeve also having a first edge and a second edge opposite the first edge, the first and second edges releasably coupled to each other through two straps, the first and second edges sized to extend along a majority of a forearm of a user when the sleeve is wrapped around the forearm;
   an inflatable bladder comprising PVC and having an expanded state wherein the bladder is charged with the cold fluid pressurized by the pump and a collapsed state wherein the bladder is substantially empty, the inflatable bladder sized such that it is small enough that at least a portion of the bladder fits inside a palm of a contracted spastic hand of the user while the bladder is in the collapsed state and large enough that the portion is larger than the palm of the contracted spastic hand when the bladder is in the expanded state, wherein the inflatable bladder is configured to be inserted into the palm of the contracted spastic hand and inflated to exert outward force on the contracted spastic hand and open the contracted spastic hand;
   a refrigeration device that is thermoelectric; and
   a fluid reservoir comprising the cold fluid, wherein the fluid is in thermal contact with the refrigeration device and maintained within a therapeutic temperature range, the fluid furthermore in fluidic communication with the two fluid-tight cavities of the sleeve and the inflatable bladder through the electric pump, at least one valve, and at least one hose.

2. The cold therapy dynamic hand splint system of claim 1, wherein the inflatable bladder is torus-shaped when in the expanded state.

3. The cold therapy dynamic hand splint system of claim 1, wherein the inflatable bladder is semi-cylindrical when in the expanded state.

4. The cold therapy dynamic hand splint system of claim 1, further comprising a control system communicatively coupled to the pump and the refrigeration device, the control system having a thermal sensor, a pressure sensor, and a processor configured to operate the refrigeration device to keep the fluid within the therapeutic temperature range, the processor further configured to operate the pump to drive the inflatable bladder from the collapsed state to the expanded state by gradually increasing a pressure within the inflatable bladder, and maintain the expanded state for a predetermined amount of time.

5. The cold therapy dynamic hand splint system of claim 4, wherein the therapeutic temperature range is between 0° C. and 20° C.

6. A cold therapy dynamic hand splint system, comprising:
   an electric pump;
   a sleeve comprising a fluid-tight cavity filled with a cold fluid pressurized by the pump, the sleeve also having a first edge and a second edge opposite the first edge, the first and second edges releasably coupled to each other, the first and second edges sized to extend along a majority of a forearm of a user when the sleeve is wrapped around the forearm;
   an inflatable bladder having an expanded state wherein the bladder is charged with the cold fluid pressurized by the pump and a collapsed state wherein the bladder is substantially empty, the inflatable bladder sized such that it is small enough that at least a portion of the bladder fits inside a palm of a contracted spastic hand of the user while the bladder is in the collapsed state and large enough that the portion is larger than the palm of the contracted spastic hand when the bladder is in the expanded state, wherein the inflatable bladder is configured to be inserted into the palm of the contracted spastic hand and inflated to exert outward force on the contracted spastic hand and open the contracted spastic hand;
   a refrigeration device; and
   a fluid reservoir coupled to the refrigeration device and comprising the cold fluid, wherein the fluid is in thermal contact with the refrigeration device and maintained within a therapeutic temperature range, the fluid furthermore in fluidic communication with the fluid-tight cavity of the sleeve and the inflatable bladder through the electric pump and at least one hose.

7. The cold therapy dynamic hand splint system of claim 6, wherein the inflatable bladder is directly coupled to the sleeve.

8. The cold therapy dynamic hand splint system of claim 6, wherein the inflatable bladder is torus-shaped when in the expanded state.

9. The cold therapy dynamic hand splint system of claim 6, wherein the inflatable bladder is semi-cylindrical when in the expanded state.

10. The cold therapy dynamic hand splint system of claim 6, further comprising a control system communicatively coupled to the pump and the refrigeration device, the control system having a thermal sensor, a pressure sensor, and a processor configured to operate the refrigeration device to keep the fluid within the therapeutic temperature range, the processor further configured to operate the pump to drive the inflatable bladder from the collapsed state to the expanded state by gradually increasing a pressure of the cold fluid within the inflatable bladder, and maintain the expanded state for a predetermined amount of time.

11. The cold therapy dynamic hand splint system of claim 10, wherein the therapeutic temperature range is between 0° C. and 20° C.

12. A cold therapy dynamic hand splint system, comprising:
- an electric pump;
- a sleeve comprising a cold source, the sleeve sized to extend along a majority of a forearm of a user when the forearm is worn and the cold source is in thermal contact with the forearm;
- an inflatable bladder having an expanded state wherein the bladder is charged with a cold fluid pressurized by the pump and a collapsed state wherein the bladder is substantially empty, the inflatable bladder sized such that it is small enough that at least a portion of the bladder fits inside a palm of a contracted spastic hand of the user while the bladder is in the collapsed state and large enough that the portion is larger than the palm of the contracted spastic hand when the bladder is in the expanded state, wherein the inflatable bladder is configured to be inserted into the palm of the contracted spastic hand and inflated to exert outward force on the contracted spastic hand and open the contracted spastic hand; and
- a fluid reservoir comprising the cold fluid, wherein the fluid is within a therapeutic temperature range and in thermal contact with the contracted spastic hand through the inflatable bladder while the bladder is in the expanded state, the fluid furthermore in fluidic communication with the inflatable bladder through the electric pump and at least one hose.

13. The cold therapy dynamic hand splint system of claim 12, wherein the cold source comprises one sealed cold pack releasably coupled to the sleeve or a plurality of sealed cold pack releasably coupled to the sleeve.

14. The cold therapy dynamic hand splint system of claim 12, wherein the inflatable bladder is torus-shaped when in the expanded state.

15. The cold therapy dynamic hand splint system of claim 12, wherein the inflatable bladder is semi-cylindrical when in the expanded state.

16. The cold therapy dynamic hand splint system of claim 12, wherein the fluid reservoir comprises an opening to receive ice water, and wherein the cold fluid is ice water.

17. The cold therapy dynamic hand splint system of claim 12, further comprising a refrigeration device coupled to the fluid reservoir and the pump, and in thermal contact with the cold fluid, wherein the refrigeration device maintains the cold fluid within the therapeutic temperature range.

18. The cold therapy dynamic hand splint system of claim 12, wherein the cold source is a fluid-tight cavity filled with the cold fluid pressurized by the pump, the fluid-tight cavity in fluidic communication with the fluid reservoir through the pump and at least one hose.

19. The cold therapy dynamic hand splint system of claim 12, wherein the therapeutic temperature range is between 0° C. and 20° C.

20. The cold therapy dynamic hand splint system of claim 12, further comprising a control system communicatively coupled to the pump and the refrigeration device, the control system having a thermal sensor, a pressure sensor, and a processor configured to operate the refrigeration device to keep the fluid within the therapeutic temperature range, the processor further configured to operate the pump to drive the inflatable bladder from the collapsed state to the expanded state by gradually increasing a pressure of the cold fluid within the inflatable bladder, and maintain the expanded state for a predetermined amount of time.

* * * * *